United States Patent [19]

Snyder, Jr.

[11] 4,002,660
[45] Jan. 11, 1977

[54] S-(4-CHLOROPHENYL)-3-ARYL-3-HYDROXYPROPANETHIOATES

[75] Inventor: Harry R. Snyder, Jr., Norwich, N.Y.

[73] Assignee: Morton-Norwich Products, Inc., Norwich, N.Y.

[22] Filed: Mar. 8, 1976

[21] Appl. No.: 664,868

[52] U.S. Cl. .............................. 260/455 R; 424/301
[51] Int. Cl.² ....................................... C07C 153/07
[58] Field of Search ............................... 260/455 R

[56] References Cited

UNITED STATES PATENTS 3,903,134  9/1975  Diamond ...................... 260/455 R Primary Examiner—Lewis Gotts
Assistant Examiner—D. R. Phillips
Attorney, Agent, or Firm—Anthony J. Franze

[57] ABSTRACT

A series of S-(4-Chlorophenyl)-3-aryl-3-hydroxypropanethioates are effective as antibacterial agents.

8 Claims, No Drawings

S-(4-CHLOROPHENYL)-3-ARYL-3-HYDROXY-PROPANETHIOATES

This invention relates to chemical compounds; particularly a series of S-(4-chlorophenyl)-3-aryl-3-hydroxypropanethioates of the formula:

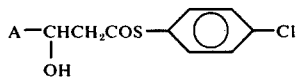

wherein A is phenyl, 4-methylphenyl, 4-ethylphenyl, 4-chlorophenyl, 2,4-dichlorophenyl, 3,4-dichlorophenyl or 3-chloro-4-methylphenyl.

These compounds are prepared by treating the 3-aryl-3-hydroxypropanoic acid with 4-chlorobenzenethiol in the presence of dicyclohexylcarbodiimide in an inert solvent such as dichloromethane.

In order that this invention may be readily available to and understood by those skilled in the art, the following examples are supplied:

EXAMPLE I

S-(4-Chlorophenyl)-3-Hydroxy-3-phenylpropanethioate

A. Preparation of 3-Hydroxy-3-phenylpropanoic Acid

Ethyl 3-hydroxy-3-phenylpropanoate (19 g, 0.1 mole) was refluxed in a solution of KOH (10 g, 0.2 mole) in ethanol for two hours. The solvent was removed in vacuo and the residue was dissolved in $H_2O$. The $H_2O$ solution was extracted with ethyl ether, then acidified with 37% hydrochloric acid. The oily product was extracted out with chloroform and the chloroform was removed in vacuo to yield 10 g (62.5%).

The residue was crystallized two times from a hexane/benzene mixture to give an analytical sample of 3 g, m.p. 89°–91°.

Anal. Calcd. for $C_9H_{10}O_3$: C, 65.06; H, 6.07. Found: C, 65.09; H, 6.13.

B. Preparation of S-(4-Chlorophenyl)-3-Hydroxy-3-phenylpropanethioate

3-Hydroxy-3-phenylpropanoic acid (30.0 g, 0.18 mole) was dissolved in methylene dichloride (600 ml) together with 4-chlorobenzenethiol (26.0 g, 0.18 mole). The solution was stirred while cyclohexylcarbodiimide (36 g, 0.18 mole) dissolved in some $CH_2Cl_2$ was added in one portion. There was a rapid, exothermic reaction with the formation of a white precipitate. The reaction mixture was stirred at room temperature for four hours and then filtered. The urea was washed with $CH_2Cl_2$. The washings and filtrate were combined and the solvent was removed under reduced pressure. The crude product was recrystallized from a benzenehexane mixture (Darco) to yield 31.7 g (60%), m.p. 103°–105° C.

An analytical sample was prepared by recrystallization from a benzene-hexane mixture, m.p. 105°–106° C.

Anal. Calcd. for $C_{15}H_{13}ClO_2S$: C, 61.53; H, 4.48; Cl, 12.11. Found: C, 61.86; H, 4.54; Cl, 12.08, 12.00.

EXAMPLE II

S-(4-Chlorophenyl) 3-Hydroxy-3-(4-methylphenyl)propanethioate

A. Preparation of 3-Hydroxy-3-(4-methylphenyl)propanoic Acid

A 5 liter, three-neck flask, equipped with a stirrer, condenser with a drying tube, and an equalizing dropping funnel was dried by flamming with a bunsen burner. The flask was then charged with 70 g (1.1 gram-atom) of zinc dust. To this was added dropwise a mixture of 120 g (1.0 mole) of 4-tolualdehyde and 120 ml (1.1 mole) of ethyl bromacetate in 100 ml of anhydrous ether and 1000 ml of dry benzene. To initiate the reaction about 50 ml of the mixture was added to the zinc and the mixture was heated to reflux. Reflux was continued throughout the addition and overnight.

The mixture was cooled and decanted from the zinc. The benzene solution was extracted with 600 ml of 10% sulfuric acid, 2 × 50 ml of 10% sodium carbonate solution, 250 ml of 5% sulfuric acid, and 250 ml of water. The benzene layer was dried over magnesium sulfate and filtered. The filtrate was evaporated in vacuo to leave an oily residue.

The oily residue from the above reaction was treated with a solution of 80 g (1.2 mole) of 85% potassium hydroxide in 1500 ml of ethanol. The mixture was refluxed for 6 hrs and was evaporated in vacuo. The residue was slurried with 1.3 liters of water and was extracted with ether. The aqueous layer was made acidic with concentrated hydrochloric acid and was extracted with 3 × 500 ml of chloroform. The chloroform extracts were dried over magnesium sulfate and were filtered. The filtrate was evaporated in vacuo to leave a solid residue. The product was recrystallized from a benzene-hexane mixture (Darco) to give a cream colored solid melting at 85°–88° in a yield of 125 g (70% from the aldehyde).

Several recrystallizations of a sample from a benzene-hexane mixture raised the melting point to 88°–90°.

Anal. Calcd. for $C_{10}H_{12}O_3$: C, 66.65; H, 6.71. Found: C, 66.53; H, 6.66.

B. Preparation of S-(4-Chlorophenyl) 3-Hydroxy-3-(4-methylphenyl)propanethioate

To a solution of A. (36.0 g, 0.2 mole) and 4-chlorobenzenethiol (29.0 g, 0.2 mole) in methylene dichloride (600 ml) was added a solution of cyclohexylcarbodiimide (41.0 g, 0.2 mole) in $CH_2Cl_2$ in one portion with stirring. There was an immediate exothermic reaction with the formation of a white precipitate. The mixture was stirred at room temperature for four hours and filtered. The filtrate was evaporated to dryness under reduced pressure. The crude product was recrystallized from cyclohexane to yield 45.0 g (73.6%), m.p. 107°–110° C.

an analytical sample was prepared by recrystallization from a benzene-hexane mixture (Darco), m.p. 113°–114° C.

Anal. Calcd. for $C_{16}H_{15}ClO_2S$: C, 62.64; H, 4.93; Cl, 11.56. Found: C, 62.92; H, 4.97; Cl, 11.66.

EXAMPLE III

S-(4-Chlorophenyl) 3-(4-Ethylphenyl)-3-hydroxypropanethioate

A. Preparation of 3-(4-Ethylphenyl)-3-hydroxypropanoic Acid

A 2 liter, three-neck flask, equipped with a stirrer, condenser with a drying tube, and an equalizing dropping funnel was dried by flamming with a bunsen burner. The flask was then charged with 40 g (0.62 gram-atom) of zinc dust. To this was added dropwise a mixture of 67 g (0.5 mole) of 4-ethyl-benzaldehyde and 68.6 ml (0.62 mole) of ethyl bromoacetate in 20 ml of anhydrous ether and 200 ml dry benzene at such a rate as to maintain a reflux. To initiate the reaction about 15 ml of the mixture was added and was heated to reflux. Reflux was continued for 6 hours and the solution was decanted from the zinc. The benzene was extracted with 300 ml of 10% sulfuric acid, 2 × 50 ml of 10% sodium carbonate, 200 ml of 5% sulfuric acid, 200 ml of water. The benzene was then dried over magnesium sulfate. The drying agent was filtered and the filtrate was evaporated in vacuo to leave on oil.

To 66 g (0.3 mole) of the residue from the above preparation was added a solution of 12 g (0.4 mole) of 85% potassium hydroxide in ethanol and was refluxed for 16 hrs. The mixture was concentrated in vacuo and the residue was dissolved in water and was extracted with ether. The aqueous solution was acidified with concentrated hydrochloric acid and was extracted with chloroform. The chloroform extracts were dried over magnesium sulfate. After filtering the drying agent the filtrate was concentrated in vacuo. The solid residue was recrystallized from a hexane-benzene mixture to give the product melting at 73°–75° in a yield of 26 g (45%).

Additional recrystallizations raised the melting point to 74°–75°.

Anal. Calcd. for $C_{11}H_{14}O_3$: C, 68.02; H, 7.27. Found: C, 68.11; H, 7.25.

B. Preparation of S-(4-Chlorophenyl) 3-(4-Ethylphenyl)-3-hydroxypropanethioate

A solution of A. (39.0 g, 0.2 mole) and 4-chlorobenzenethiol (29.0 g, 0.2 mole) in methylene dichloride (ca 600 ml) was stirred while cyclohexylcarbodiimide (41.0 g, 0.2 mole) dissolved in a small amount of $CH_2Cl_2$ was added in one portion. There was an immediate exothermic reaction with the formation of a white precipitate. The reaction mixture was stirred at room temperature for 4 hours and filtered to remove the urea. The filtrate was evaporated to dryness under reduced pressure. The residue was recrystallized from methanol to yield 38.0 g (59.4%), m.p. 114°–117° C.

An analytical sample was prepared by recrystallization from methanol (Darco), m.p. 121°–123° C.

Anal. Calcd. for $C_{17}H_{17}ClO_2S$: C, 63.64; H, 5.34; Cl, 11.05. Found: C, 63.36; H, 5.22; Cl, 11.12.

EXAMPLE IV

S-(4-Chlorophenyl) 3-(4-Chlorophenyl)-3-hydroxypropanethioate

A solution of 3-(4-chlorophenyl)-3-hydroxypropanoic acid (40.0 g, 0.2 mole) and 4-chlorobenzenethiol (29.0 g, 0.2 mole) in methylenedichloride (ca 600 ml) was stirred while cyclohexylcarbodiimide (41.9 g, 0.2 mole) dissolved in a small amount of $CH_2Cl_2$ was added in one portion. There was an immediate very exothermic reaction with the formation of a white precipitate. Once subsided, the reaction mixture was stirred at room temperature for four hours. The mixture was filtered and the filtrate was evaporated to dryness under reduced pressure to yield a white solid. The solid was recrystallized from a benzene-hexane mixture to yield 43.0 g (66%), m.p. 83°–87° C. The sample was recrystallized from a benzene-hexane mixture (Darco) to yield 26.0 g, m.p. 92°–93° C.

An analytical sample was prepared by recrystallization from a benzene-hexane mixture, m.p. 93°–94° C.

Anal. Calcd. for $C_{15}H_{12}Cl_2O_2S$: C, 55.06; H, 3.70; Cl, 21.51. Found: C, 55.45; H, 3.84; Cl, 21.40, 21.50.

EXAMPLE V

S-(4-Chlorophenyl) 3-(2,4-Dichlorophenyl)-3-hydroxypropanethioate

A. Preparation of 3-(2,4-Dichlorophenyl)-3-hydroxypropanoic Acid

A 1 liter, three-neck flask, equipped with a stirrer, condenser with a drying tube, and an equalizing dropping funnel was dried by flamming with a bunsen burner. The flask was then charged with 28 g (0.42 mole) of zinc dust. To this was added dropwise a mixture of 35 g (0.2 mole) of 2,4-dichlorobenzaldehyde and 46 ml (0.42 mole) of ethyl bromoacetate in 20 ml of anhydrous ether and 200 ml of dry benzene at such a rate as to maintain a reflux. About 20 ml of the mixture was added at first and was heated to reflux to initiate the reaction. Reflux was continued for 6 hours. Filtered the mixture and extracted the filtrate with 120 ml of 10% sodium carbonate, 50 ml of 5% sulfuric acid and 50 ml of water. The benzene solution was then dried over magnesium sulfate and filtered. The filtrate was evaporated in vacuo to leave an oily residue.

The residue obtained from the above preparation was treated with a solution of 16 g (0.25 mole) of 85% potassium hydroxide in 1500 ml of ethanol and was refluxed for 6 hrs. The mixture was evaporated in vacuo and the residue was dissolved in water. The aqueous solution was then acidified with concentrated hydrochloric acid. This was then extracted with chloroform and the chloroform extracts were dried over magnesium sulfate. The drying agent was filtered and the filtrate was evaporated in vacuo to leave the product as cream colored needles melting at 120°–125° in a yield of 32 g (68%).

Two recrystallizations of a sample from benzene raised the melting point to 124°–125°.

Anal. Calcd. for $C_9H_8Cl_2O_3$: C, 45.98; H, 3.43; Cl, 30.17. Found: C, 46.07; H, 3.55; Cl, 30.15; 30.27.

B. Preparation of S-(4-Chlorophenyl) 3-(2,4-Dichlorophenyl)-3-hydroxypropanethioate A solution of A. (47.0 g, 0.2 mole) and 4-chlorobenzenethiol (29.0 g, 0.2 mole) in methylenedichloride (600 ml) was stirred at room temperature. A solution of cyclohexylcarbodiimide (41.0 g, 0.2 mole) in a small amount of $CH_2Cl_2$ was added in one portion. There was an exothermic reaction with the formation of a white precipitate. The mixture was stirred for four hours at room temperature and then filtered. The filtrate was evaporated to dryness under reduced pressure to leave a white solid. The crude material was recrystallized from a benzene-hexane mixture to yield 30.0 g (41.5%), m.p. 70°–74° C.

An analytical sample was prepared by recrystallization from methanol, m.p. 78°–79° C.

Anal. Calcd. for $C_{15}H_{11}Cl_3O_2S$: C, 49.81; H, 3.97; Cl, 29.41. Found: C, 49.74; H, 3.03; Cl, 29.63; 29.54.

EXAMPLE VI

S-(4-Chlorophenyl) 3-(3,4-Dichlorophenyl)-3-hydroxypropanethioate

A. Preparation of 3-(3,4-Dichlorophenyl)-3-hydroxypropanoic Acid

A 5 liter, three-neck flask, equipped with a stirrer, condenser with a drying tube, and an equalizing dropping funnel was dried by flamming with a bunsen burner. The flask was charged with 90 g (1.35 gramatoms) of zinc dust. To this was added dropwise a mixture of 175 g (1.0 mole) of 3,4-dichlorobenzaldehyde and 150 ml (1.3 moles) of ethyl bromoacetate in 100 ml of anhydrous ether and 1000 ml of dry benzene at such a rate as to maintain a reflux.

To initiate the reaction about 50 ml of the mixture was added and was heated to reflux. Reflux was continued for 6 hrs. The solution was decanted from the zinc and the benzene was extracted with 60 ml of 10% sulfuric acid, 2 × 500 ml of 10% sodium carbonate, 250 ml of 5% sulfuric acid, 250 ml water. The organic layer was dried over magnesium sulfate. After filtering the drying agent the filtrate was concentrated in vacuo to leave an oily residue.

The oily residue from the above preparation was treated with a solution of 80 g (1.2 moles) of 85% potassium hydroxide in 1500 ml of ethanol. The mixture was refluxed for 6 hrs and was evaporated in vacuo. The residue was dissolved in water and was extracted with ether. The aqueous layer was acidified with concentrated hydrochloric acid and was extracted with 3 × 500 ml of chloroform. The chloroform extracts were dried over magnesium sulfate. The drying agent was filtered and the filtrate was evaporated in vacuo to leave a solid residue which was slurried in hexane and collected by filtration in a yield of 170 g (77%).

Two recrystallizations of a sample from a benzene-hexane mixture gave colorless platelets melting at 74°–75°.

Anal. Calcd. for $C_9H_8Cl_2O_3$: C, 45.98; H, 3.43; Cl, 30.17. Found: C, 45.98; H, 3.43; Cl, 30.37; 30.19.

B. Preparation of S-(4-Chlorophenyl) 3-(3,4-Dichlorophenyl)-3-hydroxypropanethioate A solution of A. (47.0 g, 0.2 mole) and 4-chlorobenzenethiol (29.0 g, 0.2 mole) in methylenedichloride (600 ml) was stirred at room temperature while cyclohexylcarbodiimide (41.0 g, 0.2 mole) dissolved in a small amount of $CH_2Cl_2$ was added in one portion. There was an immediate very exothermic reaction with the formation of a white precipitate. The reaction mixture was stirred for four hours and then filtered. The filtrate was evaporated to dryness under reduced pressure to leave a white solid. The crude material was recrystallized from a benzene-hexane mixture to yield 26.0 g (36.2%), m.p. 87°–90° C.

An analytical sample was prepared by several recrystallizations from hexane, m.p. 97°–98° C.

Anal. Calcd. for $C_{15}H_{11}Cl_3O_2S$: C, 49.81; H, 3.07; Cl, 29.41. Found: C, 50.21; H, 3.18; Cl, 29.11.

EXAMPLE VII

S-(4-Chlorophenyl) 3-(3-Chloro-4-methylphenyl)-3-hydroxypropanethioate

A. Preparation of 3-(3-Chloro-4-methylphenyl)-3-hydroxypropanoic Acid

A 5 liter, three-neck flask, equipped with a stirrer, condenser with a drying tube, and an equalizing dropping funnel was dried by flamming with a bunsen burner. The flask was charged with 90 g (1.35 gramatom) of zinc dust. To this was added dropwise a mixture of 154 g (1.0 mole) of 3-chloro-4-methylbenzaldehyde and 150 ml (1.3 moles) of ethyl bromoacetate in 100 ml of anhydrous ether and 1000 ml of dry benzene at such a rate as to maintain a reflux.

At first 50 ml of the mixture was added to the zinc and was heated to reflux to initiate the reaction. Reflux was continued for 6 hrs. The solution was decanted from the zinc and the benzene was extracted with 600 ml of 10% sulfuric acid, 2 × 500 ml of 10% sodium carbonate, 250 ml of 5% sulfuric acid, and 250 ml of water. The organic layer was dried over magnesium sulfate. After filtering the drying agent the filtrate was concentrated in vacuo to leave an oily residue.

The oil residue from the above preparation was treated with a solution of 80 g (1.2 moles) of 85% potassium hydroxide in 1500 ml of ethanol. The mixture was refluxed for 4 hrs and was then evaporated in 1500 ml of water and was extracted with ether. The aqueous layer was acidified with concentrated hydrochloric acid and was extracted with 2 × 700 ml of chloroform. The chloroform extracts were dried over magnesium sulfate. The drying agent was filtered and the filtrate was evaporated in vacuo to leave a solid residue. This was recrystallized from benzene and the product was collected as a cream colored solid melting at 80°–82° in a yield of 145 g (67.5% from the aldehyde).

Two recrystallizations of a sample from a benzene-hexane mixture gave colorless platelets melting at 85°–86°.

Anal. Calcd. for $C_{10}H_{11}ClO_3$: C, 55.95; H, 5.17; Cl, 16.52. Found: C, 56.12; H, 5.22; Cl, 16.31; 16.32.

B. Preparation of S-(4-Chlorophenyl) 3-(3-Chloro-4-methylphenyl)-3-hydroxypropanethioate A solution of A. (43.1 g, 0.2 mole) and 4-chlorobenzenethiol (29.0 g, 0.2 mole) in methylenedichloride (ca 600 ml) was stirred at room temperature. A solution of cyclohexylcarbodiimide (41.0 g, 0.2 mole) in a small amount of $CH_2Cl_2$ was added in one portion. There was an immediate very exothermic reaction with the formation of a white precipitate. After the initial reaction has subsided, the reaction mixture was stirred for 4 hours at room temperature and then filtered. The filtrate was evaporated for dryness under reduced pressure to leave a white solid. The crude material was recrystallized from a benzene-hexane mixture (Darco) to yield 13.5 g (19.8%), m.p. 80°–81°.

An analytical sample was prepared by recrystallization from a benzene-hexane mixture, m.p. 81°–83°.

Anal. Calcd. for $C_{16}H_{14}Cl_2O_2S$: C, 56.31; H, 4.14; Cl, 20.78. Found: C, 56.35; H, 4.22; Cl, 20.71.

Illustrative of the antibacterial potency of the compounds of this invention as determined in the commonly employed serial dilution technique are the results set forth in the table here below:

| | Minimum Inhibitory Concentration in mcg/mL | | | | |
|---|---|---|---|---|---|
| Example | S. aureus | Co. liquefaciens | Hc. Vaginalis | St. agalactiae | P. multocida |
| I | 6.25 | 6.25 | 12.50 | 3.13 | 6.25 |
| II | 12.50 | 12.50 | 3.10 | 3.13 | 3.13 |
| III | 6.25 | 6.25 | 6.25 | 3.13 | 6.25 |
| IV | 12.50 | 6.25 | 3.10 | 6.25 | 6.25 |
| V | 6.25 | 3.10 | 12.50 | 12.50 | 25.00 |

| Example | S. aureus | Minimum Inhibitory Concentration in mcg/ml Co. liquefaciens | He. Vaginalis | St. agalactiae | P. multocida |
|---|---|---|---|---|---|
| VI | 25.00 | 12.50 | 25.00 | 12.50 | 25.00 |
| VII | 12.50 | 12.50 | 25.00 | 12.50 | 25.00 |

What is claimed:

1. A compound of the formula:

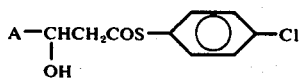

wherein A is phenyl, 4-methylphenyl, 4-ethylphenyl, 4-chlorophenyl, 2,4-dichlorophenyl, 3,4-dichlorophenyl or 3-chloro-4-methylphenyl.

2. A compound S-(4-Chlorophenyl) 3-hydroxy-3-phenylpropanethioate.

3. The compound S-(4-Chlorophenyl)3-hydroxy-3-(4-methylphenyl)propanethioate.

4. The compound S-(4-Chlorophenyl) 3-(4-ethylphenyl)-3-hydroxypropanethioate.

5. The compound S-(4-Chlorophenyl) 3-(4-chlorophenyl)-3-hydroxypropanethioate.

6. The compound S-(4-Chlorophenyl) 3-(2,4-dichlorophenyl)-3hydroxypropanethioate.

7. The compound S-(4-Chlorophenyl) 3-(3,4-dichlorophenyl)-3-hydroxypropanethioate.

8. The compound S-(4-Chlorophenyl) 3-(3-chloro-4-methylphenyl)-3-hydroxypropanethioate.

* * * * *